(12) United States Patent
Old

(10) Patent No.: US 7,589,213 B2
(45) Date of Patent: *Sep. 15, 2009

(54) THERAPEUTIC SUBSTITUTED LACTAMS

(76) Inventor: David W. Old, 13771 Typee Way, Irvine, CA (US) 92620

( * ) Notice: Subject to any disclaimer, the term of this patent is extended or adjusted under 35 U.S.C. 154(b) by 0 days.

This patent is subject to a terminal disclaimer.

(21) Appl. No.: 12/049,970

(22) Filed: Mar. 17, 2008

(65) Prior Publication Data

US 2008/0269498 A1  Oct. 30, 2008

Related U.S. Application Data

(60) Provisional application No. 60/914,546, filed on Apr. 27, 2007.

(51) Int. Cl.
C07D 277/36 (2006.01)
C07D 277/20 (2006.01)
C07D 409/12 (2006.01)

(52) U.S. Cl. .................. 548/188; 548/201; 548/202; 548/527

(58) Field of Classification Search ............ 548/188, 548/527, 202, 201; 514/422, 369, 365
See application file for complete search history.

(56) References Cited

U.S. PATENT DOCUMENTS

| 7,091,231 | B2 |  | 8/2006 | Donde | |
| 7,402,605 | B2 | * | 7/2008 | Tani et al. | 514/424 |
| 7,473,702 | B2 |  | 1/2009 | Old | |
| 7,476,747 | B2 |  | 1/2009 | Old | |
| 2003/0166668 | A1 |  | 9/2003 | Zandt | |
| 2006/0205800 | A1 | * | 9/2006 | Donde et al. | 514/381 |
| 2007/0203222 | A1 | * | 8/2007 | Old et al. | 514/422 |
| 2007/0219265 | A1 | * | 9/2007 | Old et al. | 514/422 |
| 2007/0265330 | A1 | * | 11/2007 | Old et al. | 514/422 |
| 2007/0287742 | A1 | * | 12/2007 | Old et al. | 514/424 |
| 2008/0039505 | A1 | * | 2/2008 | Old et al. | 514/342 |

FOREIGN PATENT DOCUMENTS

WO  WO 98/54180  12/1998
WO  WO 2006/098918  9/2006

OTHER PUBLICATIONS

U.S. Appl. No. 11/553,143, filed Oct. 26, 2006, Donde.
Belen'kii, L.I.; et al. Electrophilic Substitution and Transfer of Electronic Effects in Protonated and Non-Protonatetd . . . , Chemica Scripta, 1985, 25(4), 295-299.
Hermitage, Stephen A.; et al. An Efficient, Practical Approach To The Synthesis of 2,4-Disubstituted Thiazoles . . . , Organic Process Research and Development, 2001,5,37-44.

* cited by examiner

Primary Examiner—Kamal A Saeed
Assistant Examiner—Kristin Bianchi
(74) Attorney, Agent, or Firm—Kevin J. Forrestal; Allergan, Inc.

(57) ABSTRACT

Therapeutic compounds, compositions, medicaments, and methods are disclosed herein.

27 Claims, No Drawings

THERAPEUTIC SUBSTITUTED LACTAMS

CROSS REFERENCE TO RELATED APPLICATIONS

This application claims the benefit of U.S. Provisional Application Ser. No. 60/914,546 filed Apr. 27, 2007, which is hereby incorporated by reference in its entirety.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical β-adrenoreceptor antagonists have traditionally been the drugs of choice for treating glaucoma.

Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

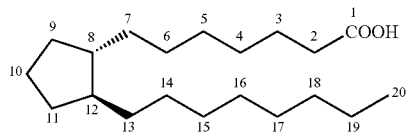

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein is a compound selected from:

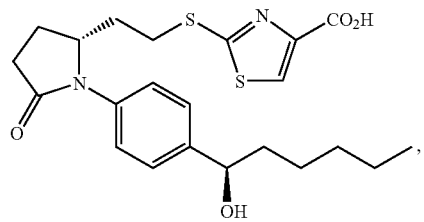

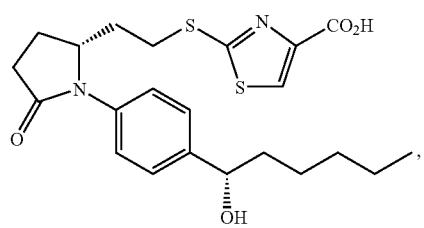

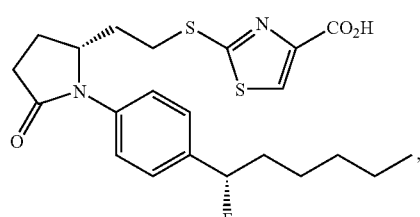

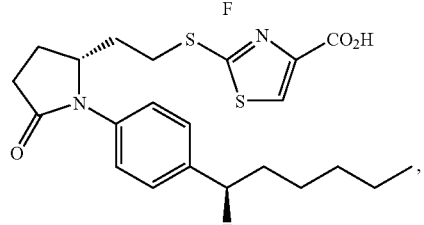

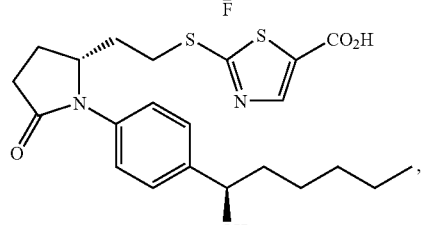

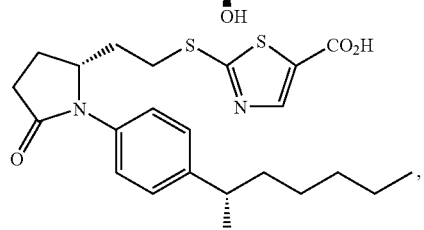

-continued
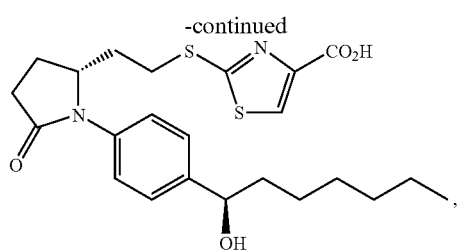
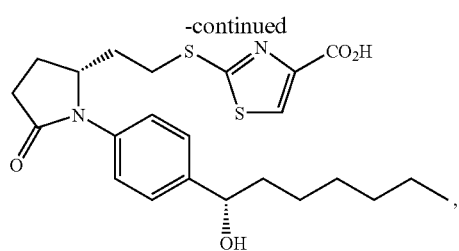
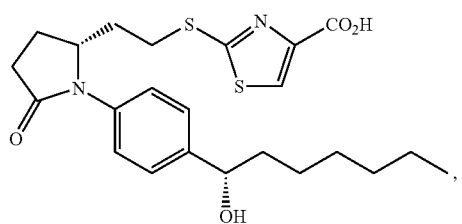
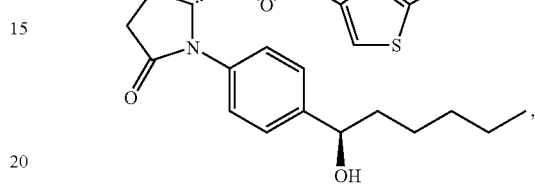
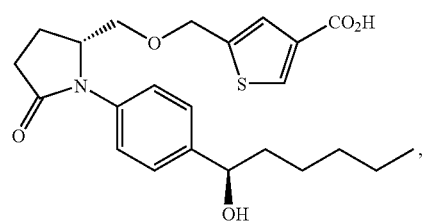
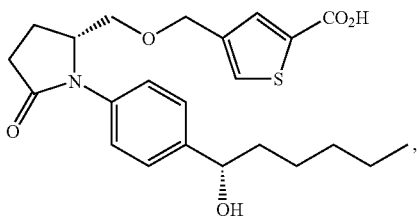
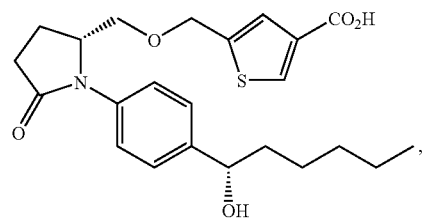
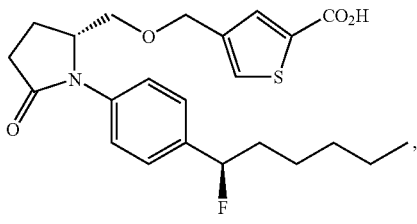
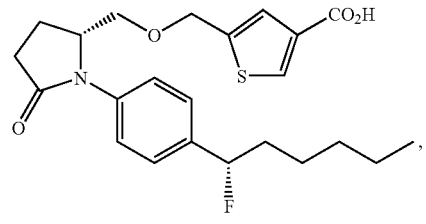
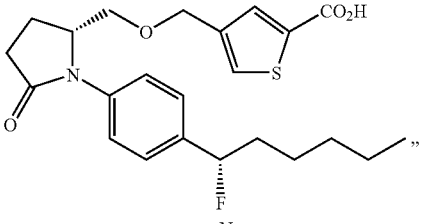
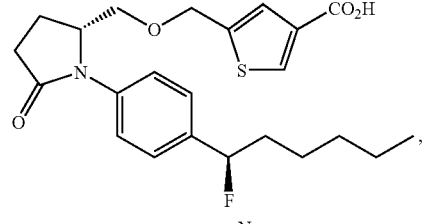
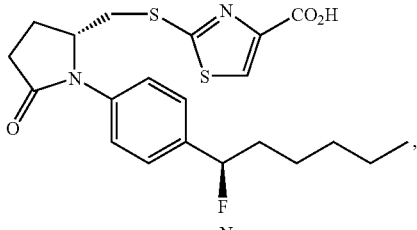
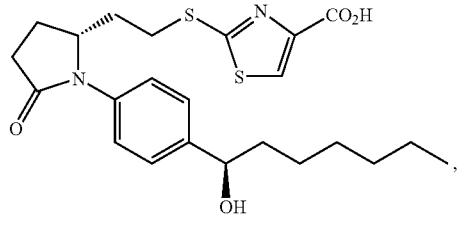
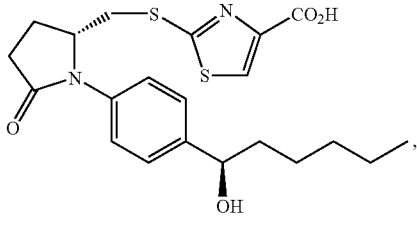

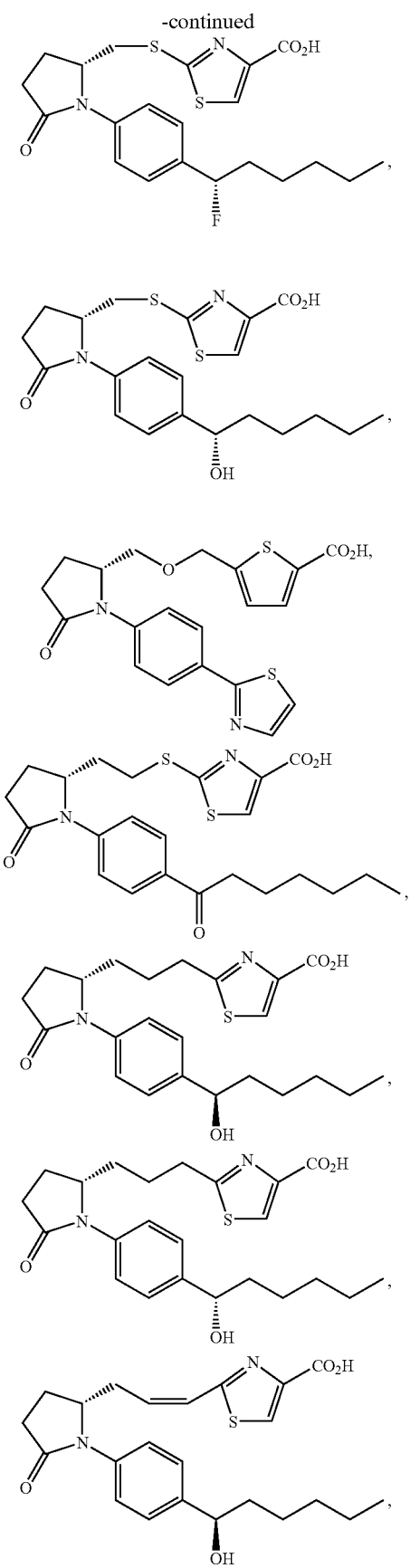

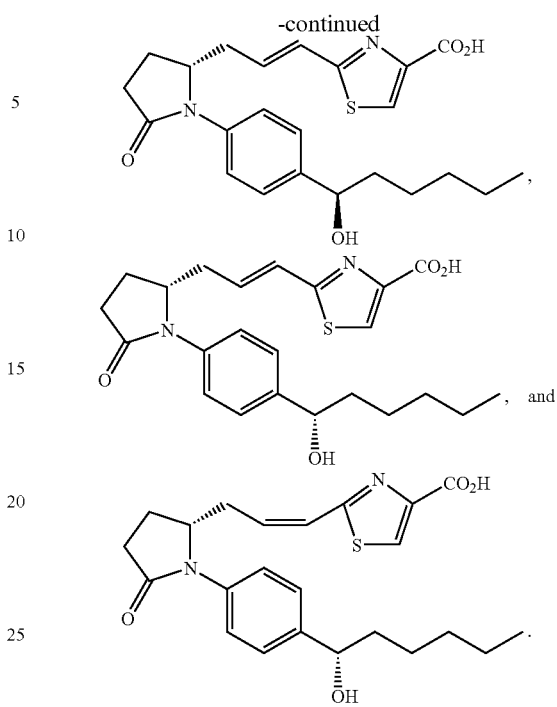

These compounds are useful for reducing intraocular pressure or treating glaucoma.

One embodiment is a method of treating glaucoma comprising administering a compound disclosed herein.

Another embodiment is a method of reducing intraocular pressure comprising administering a compound disclosed herein.

Another embodiment is use of a compound disclosed herein in the manufacture of a medicament for the reduction of intraocular pressure.

Another embodiment is use of a compound disclosed herein in the manufacture of a medicament for the treatment of glaucoma.

Unless otherwise indicated, reference to a compound should be construed broadly to include pharmaceutically acceptable salts, prodrugs, tautomers, alternate solid forms, and non-covalent complexes of a chemical entity of the depicted structure or chemical name.

A pharmaceutically acceptable salt is any salt that retains the activity of the parent compound and does not additional unacceptable deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt.

Pharmaceutically acceptable salts of acidic functional groups may be derived from organic or inorganic bases. The salt may comprise a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

A prodrug is a compound which is converted to a therapeutically active compound after administration. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. An ester may be derived from a carboxylic acid of C1 (i.e. the terminal carboxylic acid of a natural prostaglandin), or an ester may be derived from a carboxylic acid functional group on another part of the molecule, such as on a phenyl ring. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Tautomers are isomers that are in rapid equilibrium with one another. They often, but do not necessarily, include a transfer of a proton, hydrogen atom, or hydride ion.

Unless stereochemistry is explicitly depicted, a structure is intended to include every possible stereoisomer, both pure or in any possible mixture.

Alternate solid forms are different solid forms than ones that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the like.

For the purposes of this disclosure, "treat," "treating," or "treatment" refer to the use of a compound, composition, therapeutically active agent, or drug in the diagnosis, cure, mitigation, treatment, prevention of disease or other undesirable condition.

These compounds may be formulated into solid, liquid, or other types of dosage forms using methods known in the art. Both formulation of dosage forms and determination of a therapeutically effective dose can be readily made by a person of ordinary skill using routine methods.

Synthetic Methods

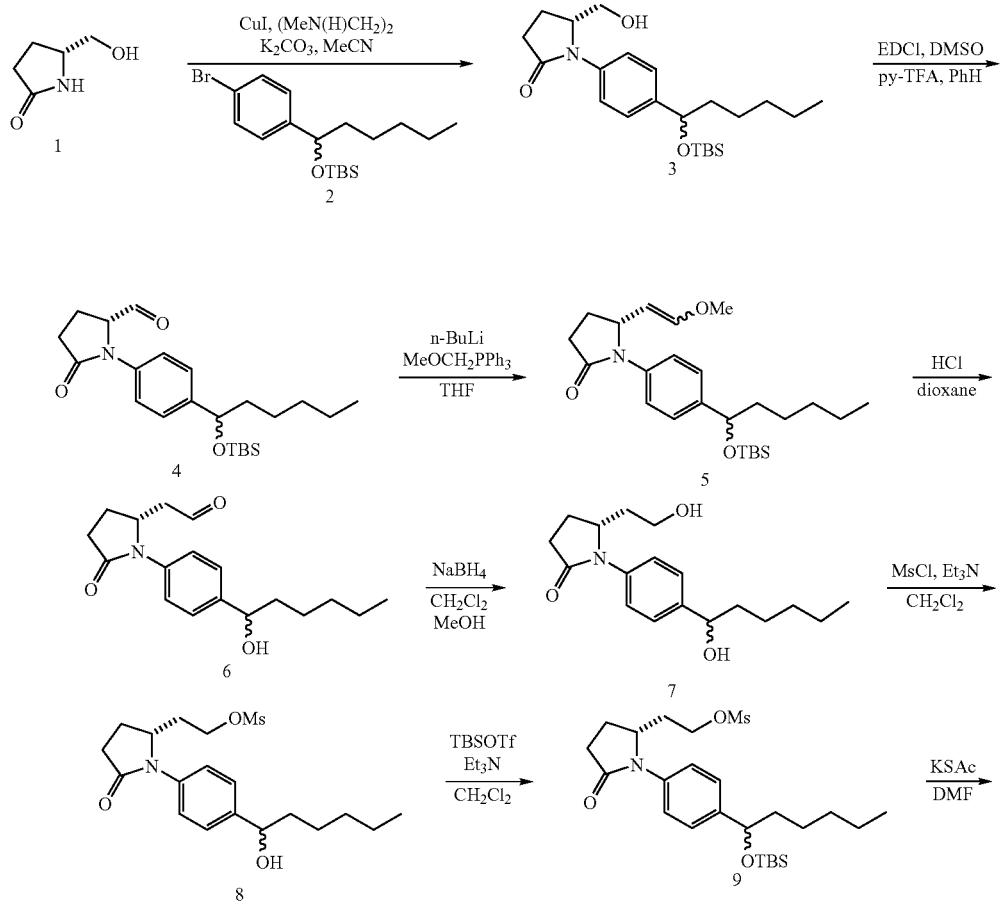

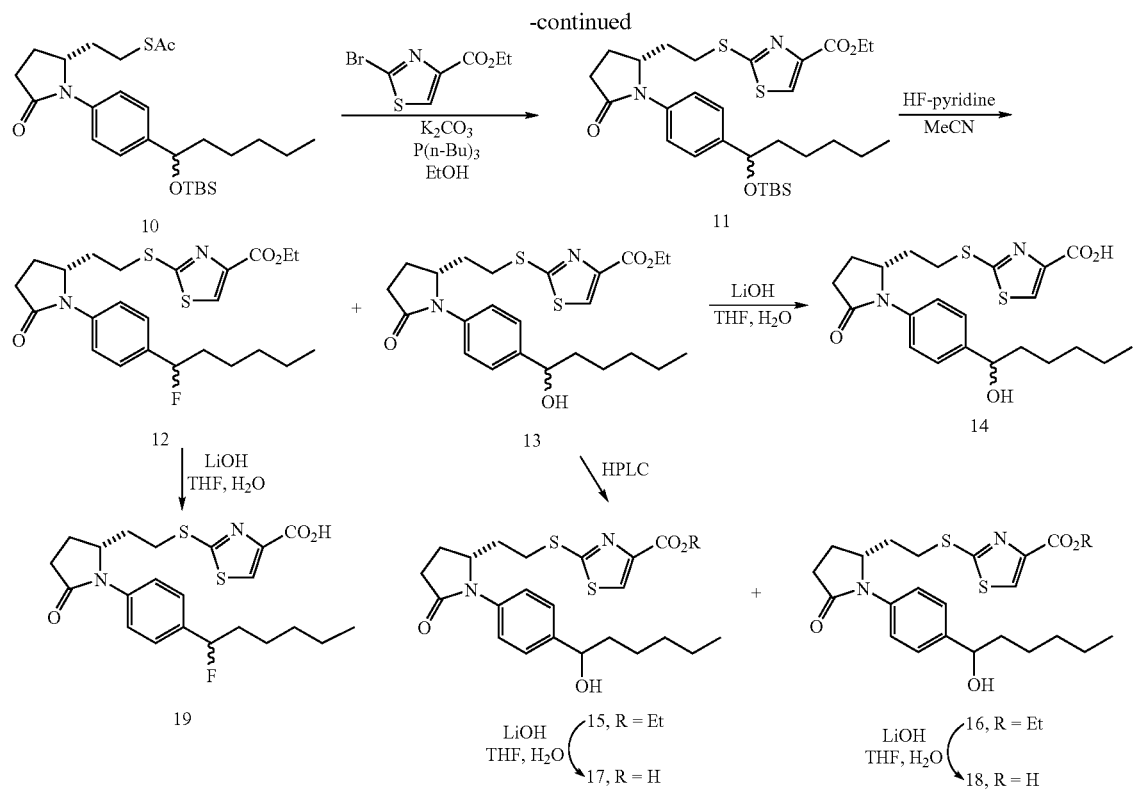

EXAMPLE 1

(R)-2-(2-(1-(4-(1-hydroxyhexyl)phenyl)-5-oxopyrrolidin-2-yl)ethylthio)thiazole-4-carboxylic acid (14)

Step 1. Arylation of 1 with 2 to Give 3

Potassium carbonate (1.53 g, 11.1 mmol), copper(I) iodide (106 mg, 0.56 mmol) and N,N'-dimethylethylene diamine (120 μL, 1.11 mmol) were added sequentially to a solution of amide 1 (726 mg, 6.74 mmol) and bromide 2 (2.06 g, 5.55 mmol) in MeCN (12.6 mL). The reaction flask was fitted with a reflux condenser, the mixture was degassed with nitrogen by evac/fill (5×) and then heated at reflux. After 4 d, the mixture was cooled, diluted with EtOAc and filtered through celite, washing with excess EtOAc. The filtrate was concentrated in vacuo. The crude residue was purified on 40 g silica (40% EtOAc/hexanes→EtOAc, gradient) to afford 1.85 g (82%) of 3 as a colorless solid.

Step 2. Oxidation of 3 to Give 4

1-(3-(Dimethylaminopropyl)-3-ethylcarbodiimide hydrochloride (EDCI, 2.63 g, 13.7 mmol) and DMSO (1.30 mL, 18.3 mmol) were added sequentially to a solution of alcohol 3 (1.85 g, 4.56 mmol) in benzene (45 mL) at room temperature under nitrogen. After 10 minutes at room temperature, pyridinium trifluoroacetate (970 mg, 5.02 mmol) was added. After 3 hours at room temperature, the solution was decanted from the oily residue and the residue was washed with benzene (3×25 mL). The combined benzene phases were concentrated in vacuo to afford crude aldehyde 4 which was taken on without further purification.

Step 3. Wittig Reaction of 4 to Give 5

A solution of n-butyllithium (1.6 M in hexane, 4.28 mL, 6.85 mmol) was added dropwise to a solution of methoxymethyl triphenylphosphonium chloride (2.35 g, 6.86 mmol) in THF (24 mL) at −78° C. After 10 minutes, the mixture was allowed to warm to room temperature. After 30 minutes, the mixture was cooled to −78° C. and added via cannula to a solution of 4 (crude from previous step, ~4.56 mmol) in THF (19.5 mL) at −78° C. After 30 minutes the reaction was allowed to warm to 0° C. After 30 minutes at 0° C., the reaction was quenched by the addition of saturated aqueous NaHCO$_3$ (100 mL), and extracted with EtOAc (3×100 mL). The combined extracts were washed with brine (100 mL), dried (Na$_2$SO$_4$), filtered and concentrated in vacuo. The crude residue was purified on 120 g silica (hexanes→EtOAc, gradient) to afford 480 mg (24% over 2 steps) of 5.

Step 4. Hydrolysis of 5 to Give 6

Aqueous HCl (1.0 N, 3.5 mL, 3.50 mmol) was added to a solution of 5 (289 mg, 0.67 mmol) in dioxane (13.5 mL). After stirring overnight at room temperature, the reaction was diluted with water (20 mL) and extracted with CH$_2$Cl$_2$ (3×35 mL). The combined extracts were washed with brine (15 mL) then dried (Na$_2$SO$_4$), filtered and concentrated in vacuo. The resulting aldehyde 6 was taken on without further purification.

Step 5. Reduction of 6 to Give 7

Sodium borohydride (50 mg, 1.32 mmol) was added in one portion to a solution of aldehyde 6 (crude from previous step, ~0.67 mmol) in CH$_2$Cl$_2$ (1.7 mL) and MeOH (1.7 mL). After 30 minutes the reaction was quenched by slow addition of 1.0 N aqueous HCl (5 mL) and concentrated in vacuo. The remaining aqueous phase was extracted with EtOAc (3×35 mL). The combined extracts were dried (Na$_2$SO$_4$), filtered and concentrated in vacuo. The crude residue was purified on 4 g silica (40% EtOAc/hexanes→EtOAc, gradient) to afford 170 mg (83% over 2 steps) of 7.

Step 6. Mesylation of 7 to Give 8

Triethylamine (155 µL, 1.12 mmol) and methanesulfonyl chloride (47 µL, 0.61 mmol) were added sequentially to a solution of diol 7 (170 mg, 0.56 mmol) in CH$_2$Cl$_2$ (5.0 mL). After 1.5 hours, saturated aqueous NaHCO$_3$ (25 mL) was added and the mixture was extracted with EtOAc (3×30 mL). The combined extracts were washed with brine (25 mL), dried (Na$_2$SO$_4$), filtered and concentrated in vacuo. The crude residue was purified on 4 g silica (60% EtOAc/hexanes→EtOAc, gradient) to afford 178 mg (83%) of 8.

Step 7. Silylation of 8 to Give 9

Triethylamine (130 µL, 0.93 mmol) and t-butyldimethylsilyl trifluoromethanesulfonate (128 µL, 0.56 mmol) were added sequentially to a solution of alcohol 8 (178 mg, 0.46 mmol) in CH$_2$Cl$_2$ (2.6 mL) at 0° C. After 20 minutes at 0° C., saturated aqueous NaHCO$_3$ (15 mL) was added and the mixture was extracted with CH$_2$Cl$_2$ (3×20 mL). The combined extracts dried (Na$_2$SO$_4$), filtered and concentrated in vacuo. The crude residue was purified on 4 g silica (40% EtOAc/hexanes→EtOAc, gradient) to afford 190 mg (82%) of 9.

Step 8. Conversion of 9 to 10

Potassium thioacetate (31 mg, 0.27 mmol) was added to a solution of mesylate 9 (91 mg, 0.18 mmol) in DMF (0.73 mL). After 45 minutes, water (10 mL) was added and the mixture was extracted with EtOAc (3×15 mL). The combined extracts were washed with brine (10 mL), dried (Na$_2$SO$_4$), filtered and concentrated in vacuo to afford thioacetate 10 which was taken on without further purification.

Step 9. Conversion of 10 to 11

Potassium carbonate (38 mg, 0.28 mmol), tributylphosphine (10 µL, 0.04 mmol) and ethyl 2-bromothiazole-4-carboxylate (46 mg, 0.19 mmol) were added to a solution of thioacetate 10 (crude from previous step, ~0.18 mmol) in absolute EtOH (0.73 mL). After stirring overnight at room temperature, the volatiles were removed under a stream of nitrogen. The resulting residue was suspended in EtOAc and filtered through celite, washing with excess EtOAc. The filtrate was concentrated in vacuo. The crude residue was purified on 4 g silica (hexanes→EtOAc, gradient) to afford 47 mg (44% over 2 steps) of 11.

Step 10. Deprotection of 11 to Give 12 and 13

HF-pyridine (0.15 mL) was added to a solution of 11 (47 mg, 0.080 mmol) in MeCN (1.6 mL) in a plastic scintillation vial at 0° C. The reaction mixture was allowed to warm to room temperature. After 1.5 hours at room temperature the reaction was quenched slowly with saturated aqueous NaHCO$_3$ (10 mL) and the mixture was extracted with EtOAc (3×15 mL). The combined extracts were washed with brine (10 mL), dried (Na$_2$SO$_4$), filtered and concentrated in vacuo. The crude residue was purified on 4 g silica (50% EtOAc/hexanes→EtOAc, gradient) to afford 2 mg (5%) of 12 and 30 mg (79%) of 13.

Step 11. Saponification of 13 to Give 14

Aqueous 1 N lithium hydroxide (0.10 mL, 0.10 mmol) was added to a solution of ester 13 (10 mg, 0.021 mmol) in THF (0.2 mL). After 18 hours at room temperature, the mixture was diluted with water (1.0 mL) and acidified with 1 N aqueous HCl (1.0 mL). The mixture was extracted with EtOAc (3×8 mL). The combined extracts were dried (Na$_2$SO$_4$), filtered and concentrated in vacuo to afford 9.4 mg (quant.) of the title compound (14).

EXAMPLE 2

(R)-2-(2-(1-(4-(1-hydroxyhexyl)phenyl)-5-oxopyrrolidin-2-yl)ethylthio)thiazole-4-carboxylic acid (17, from faster eluting (HPLC) ethyl ester)

Step 1. HPLC Separation of 13 to Give 15 and 16

The two diastereomers from example 1, step 10 (13, ~26 mg) were separated on a Waters 600 HPLC instrument employing a Waters 2996 PDA detector and a Phenomenex Luna 10µ prep silica (2) 1 column, 50 mm×250 mm (p/no. 00G-4322-V0; s/no. 356757-1). Using a flow rate of 45 mL/minutes, 60% EtOAc/Hex as the eluent for 130 minutes, followed by 75% EtOAc/Hex until complete elution, the first diastereomer (15, 11 mg) eluted at 165-179 minutes, and the second diastereomer (16, 11 mg) eluted at 180-195 minutes.

Step 2. Saponification of 15 to Give 17

In accordance with the procedure of example 1, step 11, ester 15 (10 mg, 0.021 mmol) was converted into 9 mg (96%) of the title compound (17).

EXAMPLE 3

(R)-2-(2-(1-(4-(1-hydroxyhexyl)phenyl)-5-oxopyrrolidin-2-yl)ethylthio)thiazole-4-carboxylic acid (18, from slower eluting (HPLC) ethyl ester)

In accordance with the procedure of example 1, step 11, ester 16 (10 mg, 0.021 mmol) was converted into 9 mg (96%) of the title compound (18).

EXAMPLE 4

(R)-2-(2-(1-(4-(1-fluorohexyl)phenyl)-5-oxopyrrolidin-2-yl)ethylthio)thiazole-4-carboxylic acid (19)

In accordance with the procedure of example 1, step 11, ester 12 (2 mg, 0.0042 mmol) was converted into 2 mg (quant.) of the title compound (19).

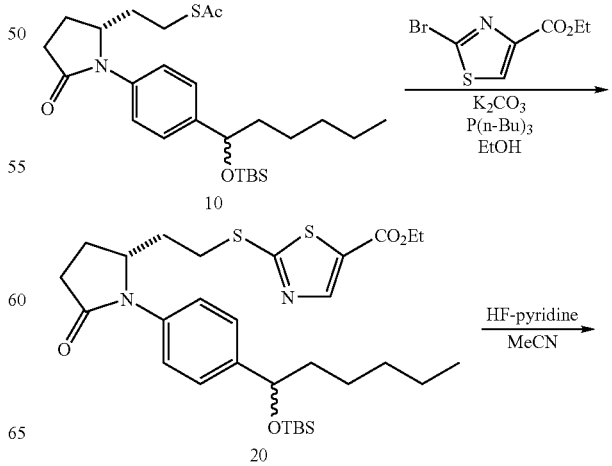

Scheme 2

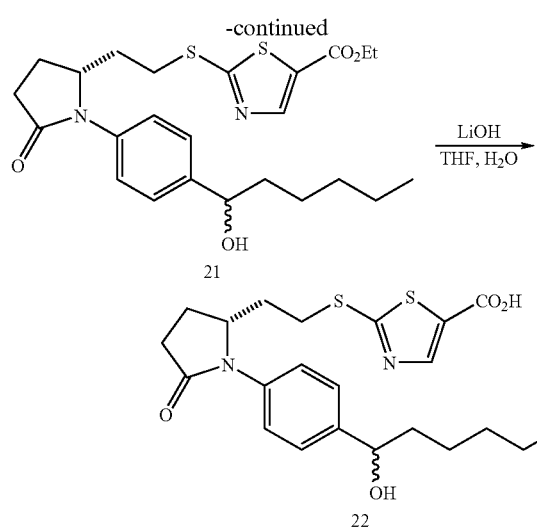

EXAMPLE 5
(R)-2-(2-(1-(4-(1-hydroxyhexyl)phenyl)-5-oxopyrrolidin-2-yl)ethylthio)thiazole-5-carboxylic acid (22)

Step 1. Conversion of 10 to 20

Ethyl 2-bromothiazole-5-carboxylate (15 µL, 0.10 mmol), tributylphosphine (5 µL, 0.02 mmol), and potassium carbonate (20 mg, 0.15 mmol), were added sequentially to a solution of thioacetate 10 (crude from example 1, step 8, 45 mg, 0.094 mmol) in absolute EtOH (0.38 mL). After stirring overnight at room temperature, the volatiles were removed under a stream of nitrogen. The resulting residue was suspended in EtOAc and then decanted and concentrated in vacuo. The crude residue was purified on 4 g silica (hexanes→EtOAc, gradient) to afford 55 mg (99%) of 20.

Step 2. Deprotection of 20 to Give 21

HF-pyridine (0.15 mL) was added to a solution of 11 (55 mg, 0.093 mmol) in MeCN (1.85 mL) in a plastic scintillation vial at 0° C. After 1 hour at 0° C., the reaction was quenched slowly with saturated aqueous $NaHCO_3$ (10 mL) and the mixture was extracted with EtOAc (3×20 mL). The combined extracts were washed with brine (10 mL), dried ($Na_2SO_4$), filtered and concentrated in vacuo. The crude residue was purified on 4 g silica (30% EtOAc/hexanes→EtOAc, gradient) to afford 27 mg (49%) of starting material 20 and 16 mg (36%) of 21.

Step 3. Saponification of 21 to Give 22

In accordance with the procedure of example 1, step 11, ester 21 (16 mg, 0.034 mmol) was converted into 15 mg (99%) of the title compound (22).

Scheme 3

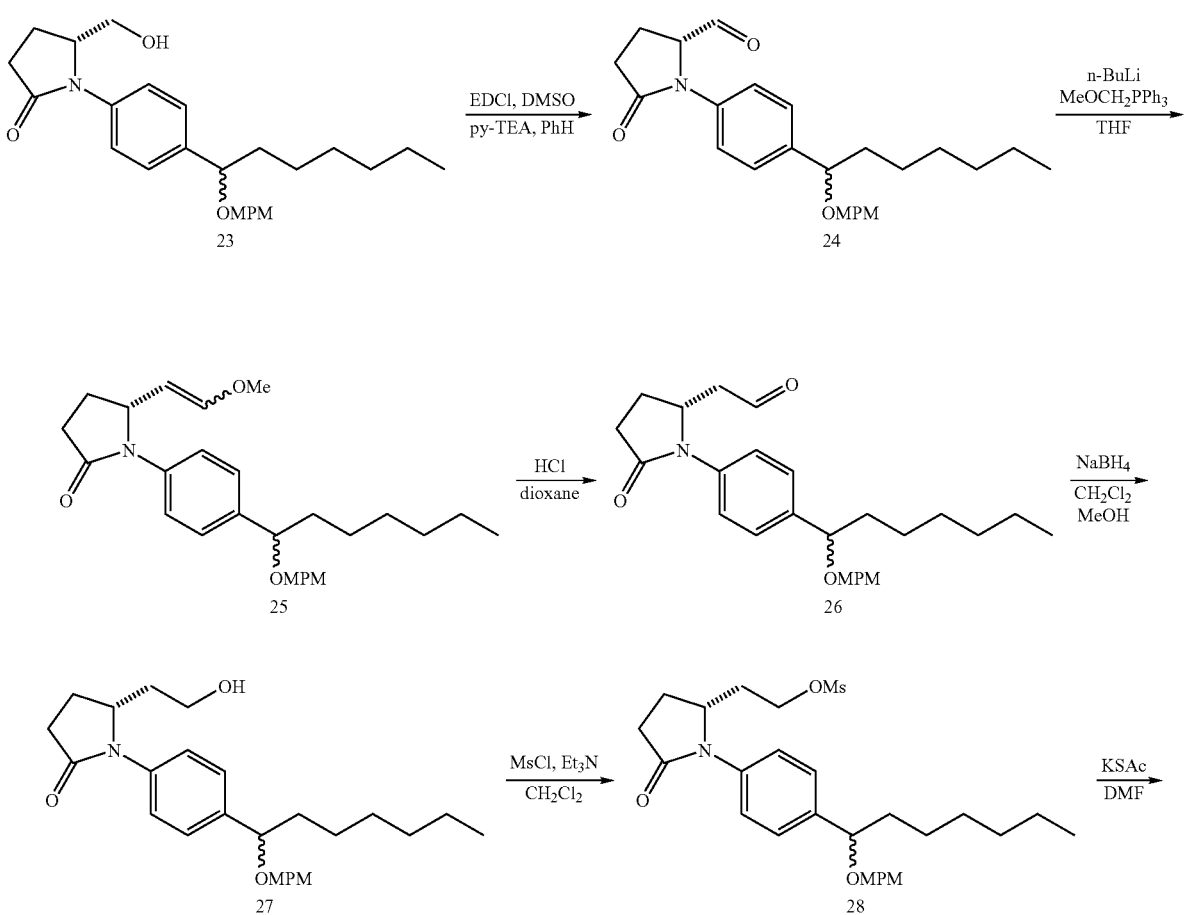

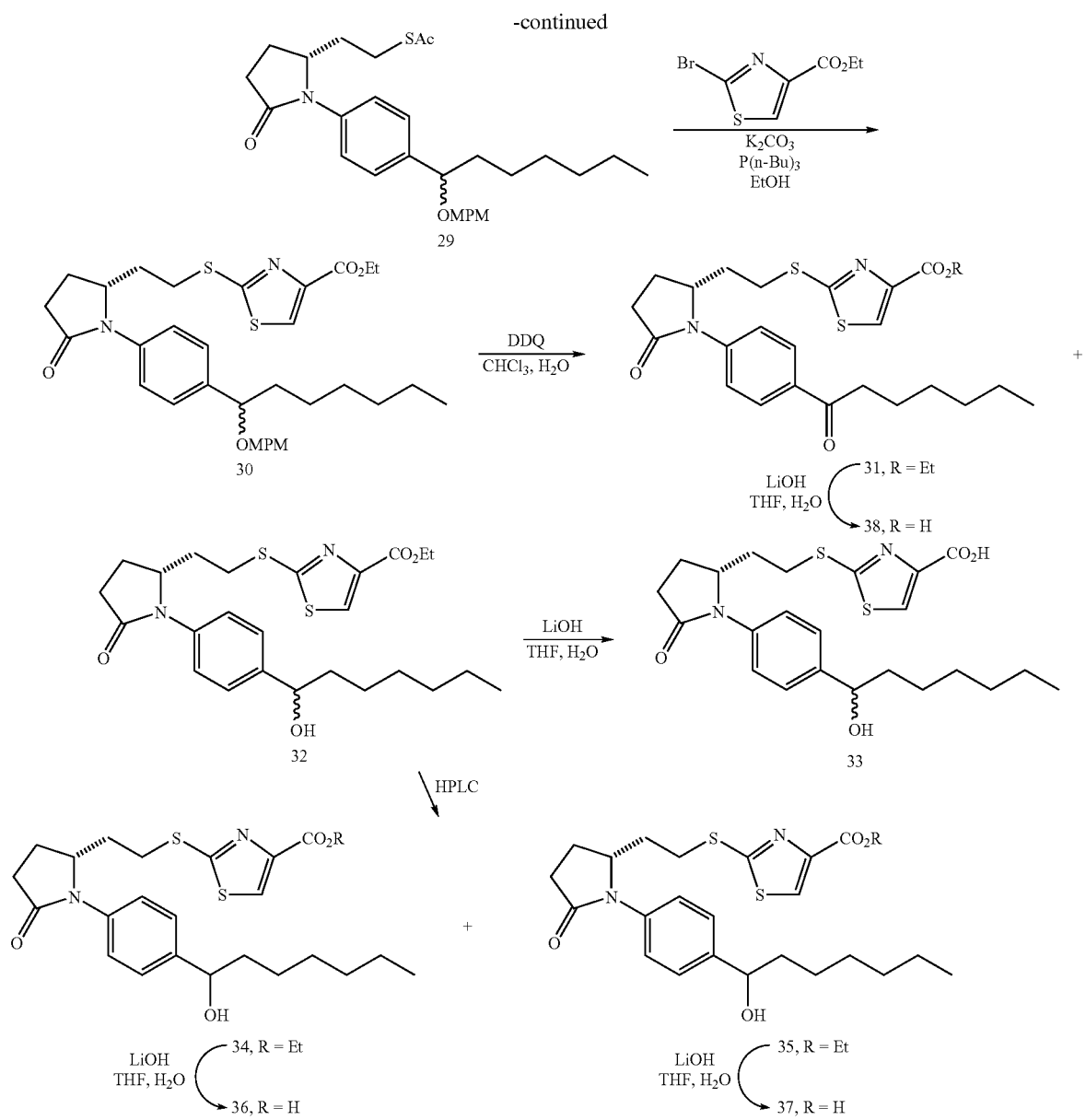

EXAMPLE 6

(R)-2-(2-(1-(4-(1-hydroxyheptyl)phenyl)-5-oxopyrrolidin-2-yl)ethylthio)thiazole-4-carboxylic acid (33)

Step 1. Oxidation of 23 to Give 24

EDCI (2.63 g, 13.7 mmol) and DMSO (1.30 mL, 18.3 mmol) were added sequentially to a solution of alcohol 23 (see WO2006/098918, 1.94 g, 4.56 mmol) in benzene (45 mL) at room temperature under nitrogen. After 10 minutes at room temperature, pyridinium trifluoroacetate (970 mg, 5.02 mmol) was added. After 3 hours at room temperature, the solution was decanted from the oily residue and the residue was washed with benzene (3×25 mL). The combined benzene phases were concentrated in vacuo to afford crude aldehyde 24 which was taken on without further purification.

Step 2. Wittig Reaction of 24 to Give 25

A solution of n-butyllithium (1.6 M in hexane, 4.28 mL, 6.85 mmol) was added dropwise to a solution of methoxymethyl triphenylphosphonium chloride (2.35 g, 6.86 mmol) in THF (24 mL) at −78° C. After 10 minutes, the mixture was allowed to warm to room temperature. After 30 minutes, the mixture was cooled to −78° C. and added via cannula to a solution of 24 (crude from previous step, ~4.56 mmol) in THF (19.5 mL) at −78° C. After 30 minutes the reaction was allowed to warm to 0° C. After 30 minutes at 0° C., the reaction was quenched by the addition of saturated aqueous NaHCO$_3$ (100 mL), and extracted with EtOAc (3×100 mL). The combined extracts were washed with brine (100 mL), dried (Na$_2$SO$_4$), filtered and concentrated in vacuo. The crude residue was purified on 120 g silica (hexanes→EtOAc, gradient) to afford 182 mg (8% over 2 steps) of 25.

Step 3. Hydrolysis of 25 to Give 26

Aqueous HCl (1.0 N, 2.0 mL, 2.0 mmol) was added to a solution of 25 (182 mg, 0.40 mmol) in dioxane (8 mL). After stirring overnight at room temperature, the reaction was diluted with water (20 mL) and extracted with $CH_2Cl_2$ (3×35 mL). The combined extracts were washed with brine (15 mL) then dried ($Na_2SO_4$), filtered and concentrated in vacuo. The resulting aldehyde 26 was taken on without further purification.

Step 4. Reduction of 26 to Give 27

Sodium borohydride (31 mg, 0.82 mmol) was added in one portion to a solution of aldehyde 26 (crude from previous step, ~0.40 mmol) in $CH_2Cl_2$ (2.0 mL) and MeOH (2.0 mL). After 30 minutes the reaction was quenched by slow addition of 1.0 N aqueous HCl (5 mL) and concentrated in vacuo. The remaining aqueous phase was extracted with EtOAc (3×30 mL). The combined extracts were washed with brine (15 mL), dried ($Na_2SO_4$), filtered and concentrated in vacuo. The crude residue was purified on 12 g silica (40% EtOAc/hexanes→EtOAc, gradient) to afford 139 mg (78% over 2 steps) of 27.

Step 5. Mesylation of 27 to Give 28

Triethylamine (88 μL, 0.63 mmol) and methanesulfonyl chloride (27 μL, 0.35 mmol) were added sequentially to a solution of diol 27 (139 mg, 0.32 mmol) in $CH_2Cl_2$ (2.9 mL). After 18 hours, saturated aqueous $NaHCO_3$ (10 mL) was added and the mixture was extracted with EtOAc (3×30 mL). The combined extracts were washed with brine (15 mL), dried ($Na_2SO_4$), filtered and concentrated in vacuo to afford mesylate 28 which was taken on without further purification.

Step 6. Conversion of 28 to 29

Potassium thioacetate (54 mg, 0.47 mmol) was added to a solution of crude mesylate 28 (crude from previous step, ~0.32 mmol) in DMF (1.3 mL). After 2.5 hours, water (20 mL) was added and the mixture was extracted with EtOAc (3×30 mL). The combined extracts were washed with water (15 mL) and brine (15 mL), dried ($Na_2SO_4$), filtered and concentrated in vacuo to afford thioacetate 29 which was taken on without further purification.

Step 7. Conversion of 29 to 30

Potassium carbonate (65 mg, 0.47 mmol), tributylphosphine (16 μL, 0.065 mmol) and ethyl 2-bromothiazole-4-carboxylate (80 mg, 0.34 mmol) were added to a solution of crude thioacetate 29 (crude from previous step, ~0.32 mmol) in absolute EtOH (1.3 mL). After stirring overnight at room temperature, the volatiles were removed under a stream of nitrogen. The resulting residue was suspended in EtOAc and filtered through celite, washing with excess EtOAc. The filtrate was concentrated in vacuo. The crude residue was purified on 12 g silica (40% ETOAc/hexanes→EtOAc, gradient) to afford 108 mg (56% over 3 steps) of 30.

Step 8. Deprotection of 30 to Give 31 and 32

2,3-Dichloro-5,6-dicyano-1,4-benzoquinone (DDQ, 44 mg, 0.19 mmol) was added to a mixture of 30 (108 mg, 0.18 mmol) in $CH_2Cl_2$ (2.2 mL) and water (0.1 mL) at 0° C. After 45 minutes at 0° C., the reaction mixture was allowed to warm to room temperature. After 45 minutes at room temperature, the reaction was quenched with saturated aqueous $NaHCO_3$ (10 mL). The mixture was extracted with EtOAc (3×15 mL). The combined extracts were washed with saturated aqueous $NaHSO_3$ (2×15 mL) and brine (15 mL) then dried ($Na_2SO_4$), filtered and concentrated in vacuo. The crude residue was purified on 4 g silica (40% EtOAc/hexanes→EtOAc, gradient) to afford 18 mg (21%) of ketone 31 and 62 mg (71%) of alcohol 32.

Step 9. Saponification of 32 to Give 33

In accordance with the procedure of example 1, step 11, ester 32 (13 mg, 0.026 mmol) was converted into 12 mg (98%) of the title compound (33).

EXAMPLE 7

(R)-2-(2-(1-(4-(1-hydroxyheptyl)phenyl)-5-oxopyrrolidin-2-yl)ethylthio)thiazole-4-carboxylic acid (36, from faster eluting (HPLC) ethyl ester)

Step 1. HPLC Separation of 32 to Give 34 and 35

The two diastereomers from example 1, step 10 (32, ~25 mg) were separated on a Waters 600 HPLC instrument employing a Waters 2996 PDA detector and a Phenomenex Luna 10μ prep silica (2) 1 column, 50 mm×250 mm (p/no. 00G-4322-V0; s/no. 356757-1). Using a flow rate of 45 mL/minutes, 70% EtOAc/Hex as the eluent for 90 minutes, followed by 75% EtOAc/Hex until complete elution, the first diastereomer (34, 10 mg) eluted at 112-125 minutes, and the second diastereomer (35, 11 mg) eluted at 125-142 minutes.

Step 2. Saponification of 34 to Give 36

In accordance with the procedure of example 1, step 11, ester 34 (10 mg, 0.02 mmol) was converted into 9 mg (95%) of the title compound (36).

EXAMPLE 8

(R)-2-(2-(1-(4-(1-hydroxyheptyl)phenyl)-5-oxopyrrolidin-2-yl)ethylthio)thiazole-4-carboxylic acid (37, from slower eluting (HPLC) ethyl ester)

In accordance with the procedure of example 1, step 11, ester 35 (10 mg, 0.02 mmol) was converted into 9 mg (95%) of the title compound (37).

EXAMPLE 9

(R)-2-(2-(1-(4-heptanoylphenyl)-5-oxopyrrolidin-2-yl)ethylthio)thiazole-4-carboxylic acid (38)

In accordance with the procedure of example 1, step 11, ester 31 (18 mg, 0.037 mmol) was converted into 16 mg (94%) of the title compound (37) after purification on 4 g silica ($CH_2Cl_2$→15% MeOH/$CH_2Cl_2$, gradient).

19

-continued

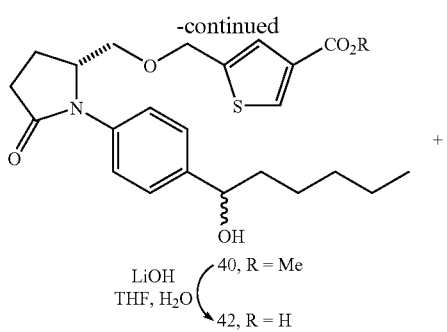

40, R = Me
42, R = H
LiOH
THF, H₂O

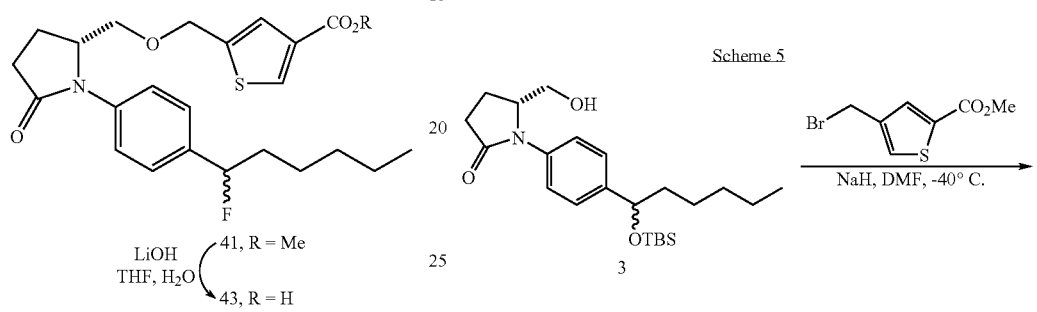

41, R = Me
43, R = H
LiOH
THF, H₂O

EXAMPLE 10

(R)-5-(((1-(4-(1-hydroxyhexyl)phenyl)-5-oxopyrrolidin-2-yl)methoxy)methyl)thiophene-3-carboxylic acid (42)

Step 1. Alkylation of 3 to Give 39

Sodium hydride (60% dispersion in oil, 26 mg, 0.65 mmol) was added to a solution of alcohol 3 (180 mg, 0.44 mmol) at 0° C. and the mixture was allowed to warm to room temperature. After 20 minutes, the mixture was cooled to −40° C. and a solution of methyl 5-(bromomethyl)thiophene-3-carboxylate (prepared analogously to the known chloride as described by M. C. Van Zandt and L. Geraci US2003/0166668; 125 mg, 0.53 mmol) in DMF (1.1 mL) was added via cannula. After 3 hours at −40° C. the reaction was quenched with 0.5 N HCl (15 mL) and extracted with EtOAc (3×25 mL). The combined extracts were washed with water (2×20 mL) and brine (20 mL) then dried (Na₂SO₄), filtered and concentrated in vacuo. The crude residue was purified on 12 g silica (hexanes→EtOAc, gradient) to afford 240 mg (97%) of 39.

Step 2. Deprotection of 39 to Give 40 and 41

HF-pyridine (0.25 mL) was added to a solution of 39 (112 mg, 0.20 mmol) in MeCN (4.0 mL) in a plastic scintillation vial at 0° C. and the reaction mixture was allowed to warm to room temperature. After 2 hours at room temperature, the reaction was quenched slowly with saturated aqueous NaHCO₃ (10 mL) and the mixture was extracted with EtOAc (3×15 mL). The combined extracts were washed with brine (10 mL), dried (Na₂SO₄), filtered and concentrated in vacuo. The crude residue was purified on 4 g silica (40% EtOAc/hexanes→EtOAc, gradient) to afford 62 mg (70%) of alcohol 40 and 3 mg (3%) of fluoride 41.

20

Step 3. Saponification of 40 to Give 42

In accordance with the procedure of example 1, step 11, ester 40 (23 mg, 0.052 mmol) was converted into 21 mg (94%) of the title compound (42).

EXAMPLE 11

(R)-5-(((1-(4-(1-fluorohexyl)phenyl)-5-oxopyrrolidin-2-yl)methoxy)methyl)thiophene-3-carboxylic acid (43)

In accordance with the procedure of example 1, step 11, ester 41 (3 mg, 0.007 mmol) was converted into 1.5 mg (52%) of the title compound (43) after purification on 4 g silica (CH₂Cl₂→10% MeOH/CH₂Cl₂, gradient).

Scheme 5

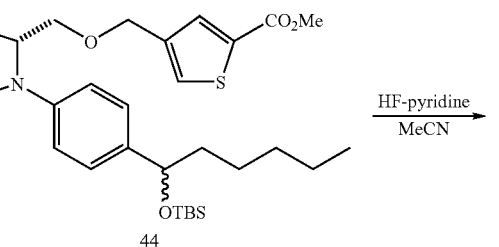

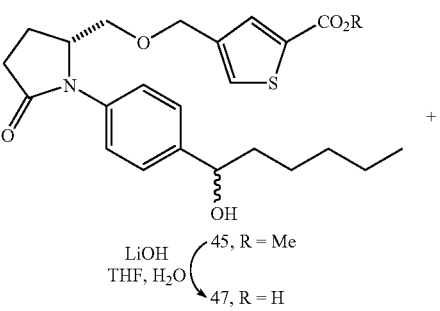

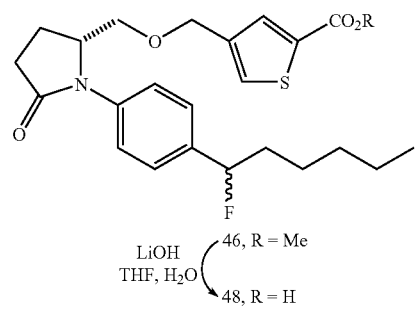

45, R = Me
47, R = H
LiOH
THF, H₂O

46, R = Me
48, R = H
LiOH
THF, H₂O

EXAMPLE 12

(R)-4-(((1-(4-(1-hydroxyhexyl)phenyl)-5-oxopyrrolidin-2-yl)methoxy)methyl)thiophene-2-carboxylic acid (47)

Step 1. Alkylation of 3 to Give 44

Sodium hydride (60% dispersion in oil, 26 mg, 0.65 mmol) was added to a solution of alcohol 3 (180 mg, 0.44 mmol) at 0° C. and the mixture was allowed to warm to room temperature. After 20 minutes, the mixture was cooled to −40° C. and a solution of methyl 4-(bromomethyl)thiophene-2-carboxylate (for a representative preparative procedure, see N. Kindon et al. WO98/054180; 125 mg, 0.53 mmol) in DMF (1.1 mL) was added via cannula. After 1 hours at −40° C. the reaction was quenched with 0.5 N HCl (15 mL) and extracted with EtOAc (3×25 mL). The combined extracts were washed with water (2×20 mL) and brine (20 mL) then dried (Na$_2$SO$_4$), filtered and concentrated in vacuo. The crude residue was purified on 12 g silica (hexanes→EtOAc, gradient) to afford 97 mg (39%) of 44.

Step 2. Deprotection of 44 to Give 45 and 46

HF-pyridine (0.20 mL) was added to a solution of 44 (97 mg, 0.17 mmol) in MeCN (3.5 mL) in a plastic scintillation vial at 0° C. and the reaction mixture was allowed to warm to room temperature. After 2 hours at room temperature, the reaction was quenched slowly with saturated aqueous NaHCO$_3$ (10 mL) and the mixture was extracted with EtOAc (3×25 mL). The combined extracts were dried (Na$_2$SO$_4$), filtered and concentrated in vacuo. The crude residue was purified on 4 g silica (40% EtOAc/hexanes→EtOAc, gradient) to afford 75 mg (97%) of alcohol 45 and 2 mg (2%) of fluoride 46.

Step 3. Saponification of 45 to Give 47

In accordance with the procedure of example 1, step 11, ester 45 (25 mg, 0.056 mmol) was converted into 22 mg (91%) of the title compound (47).

EXAMPLE 13

(R)-4-(((1-(4-(1-fluorohexyl)phenyl)-5-oxopyrrolidin-2-yl)methoxy)methyl)thiophene-2-carboxylic acid (48)

In accordance with the procedure of example 1, step 11, ester 46 (2 mg, 0.005 mmol) was converted into 1.5 mg (77%) of the title compound (48).

Scheme 6

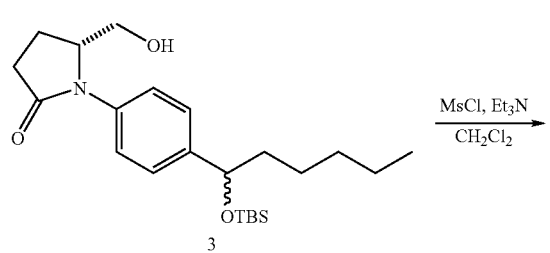

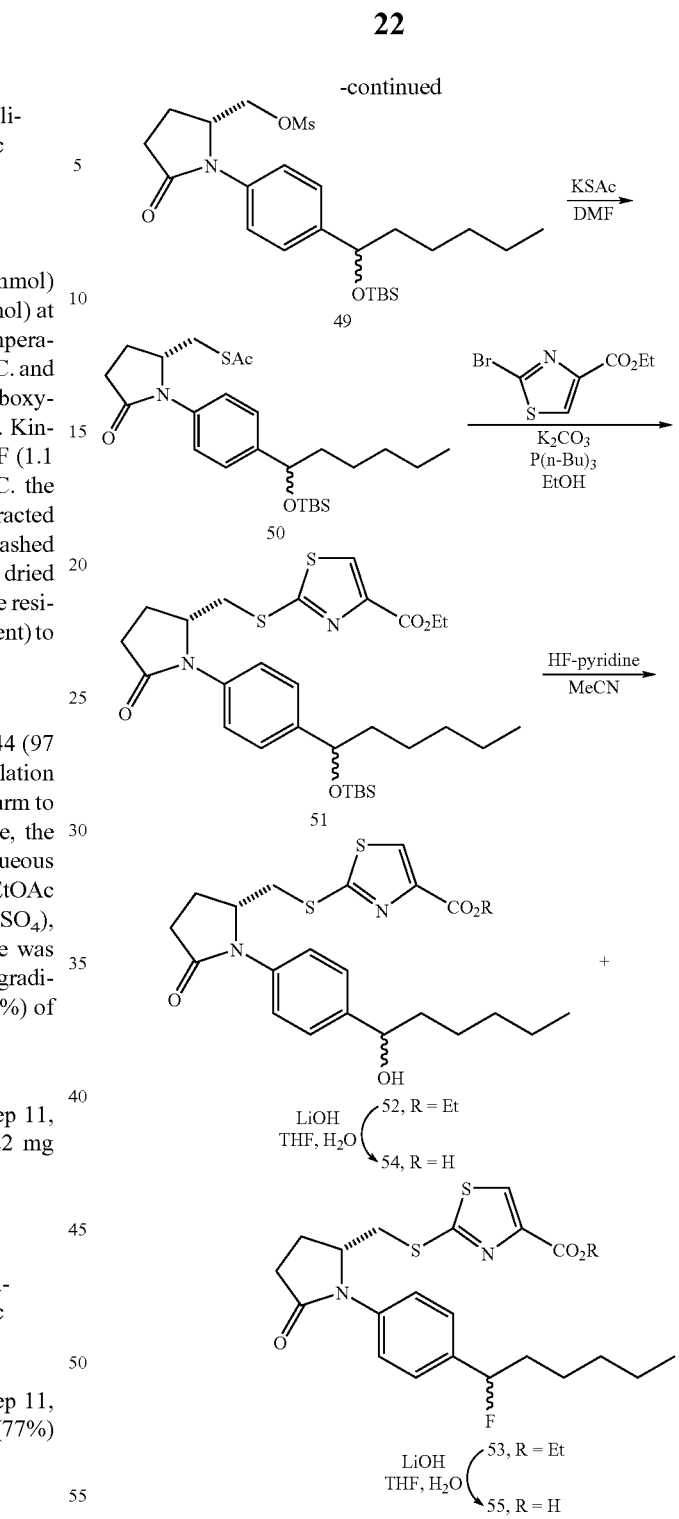

EXAMPLE 14

(R)-2-((1-(4-(1-hydroxyhexyl)phenyl)-5-oxopyrrolidin-2-yl)methylthio)thiazole-4-carboxylic acid (54)

Step 1. Mesylation of 3 to Give 49

Triethylamine (115 μL, 0.83 mmol) and methanesulfonyl chloride (36 μL, 0.46 mmol) were added sequentially to a solution of alcohol 3 (173 mg, 0.43 mmol) in CH$_2$Cl$_2$ (3.8 mL). After 2 hours, saturated aqueous NaHCO₃ (15 mL) was added and the mixture was extracted with EtOAc (3×30 mL). The combined extracts were washed with brine (15 mL), dried (Na₂SO₄), filtered and concentrated in vacuo to afford 206 mg (quant.) of mesylate 49 which solidified on standing.

Step 2. Conversion of 49 to 50

Potassium thioacetate (73 mg, 0.64 mmol) was added to a solution of mesylate 49 (206 mg, 0.43 mmol) in DMF (1.7 mL). After 3 days, water (15 mL) was added and the mixture was extracted with EtOAc (3×30 mL). The combined extracts were washed with brine (15 mL), dried (Na₂SO₄), filtered and concentrated in vacuo to afford 198 mg (quant.) of thioacetate 50 which was taken on without further purification.

Step 3. Conversion of 50 to 51

Potassium carbonate (53 mg, 0.38 mmol), tributylphosphine (13 µL, 0.05 mmol) and ethyl 2-bromothiazole-4-carboxylate (64 mg, 0.27 mmol) were added to a solution of thioacetate 50 (118 mg, 0.25 mmol) in absolute EtOH (1.0 mL). After stirring overnight at room temperature under nitrogen, the volatiles were removed under a stream of nitrogen. The resulting residue was suspended in EtOAc and filtered through celite, washing with excess EtOAc. The filtrate was concentrated in vacuo. The crude residue was purified on 12 g silica (hexanes→50% EtOAc/hexanes, gradient) to afford 101 mg (69%) of 51.

Step 4. Deprotection of 51 to Give 52 and 53

HF-pyridine (0.20 mL) was added to a solution of 51 (100 mg, 0.17 mmol) in MeCN (3.4 mL) in a plastic scintillation vial at 0° C. The reaction mixture was allowed to warm to room temperature. After 3 hours at room temperature the reaction was quenched slowly with saturated aqueous NaHCO₃ (15 mL) and the mixture was extracted with EtOAc (3×30 mL). The combined extracts were dried (Na₂SO₄), filtered and concentrated in vacuo. The crude residue was purified on 4 g silica (50% EtOAc/hexanes→EtOAc, gradient) to afford 71 mg (89%) of 52 and 5 mg (6%) of 53.

Step 5. Saponification of 52 to Give 54

In accordance with the procedure of example 1, step 11, ester 52 (10.5 mg, 0.023 mmol) was converted into 9 mg (91%) of the title compound (54).

EXAMPLE 15

(R)-2-((1-(4-(1-fluorohexyl)phenyl)-5-oxopyrrolidin-2-yl)methylthio)thiazole-4-carboxylic acid (55)

In accordance with the procedure of example 1, step 11, ester 53 (5 mg, 0.011 mmol) was converted into 4 mg (85%) of the title compound (55).

Scheme 7

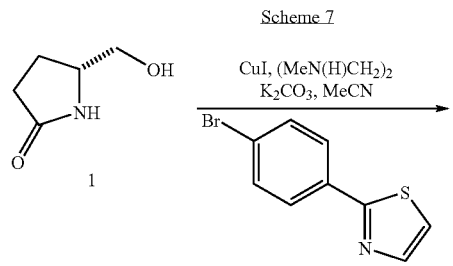

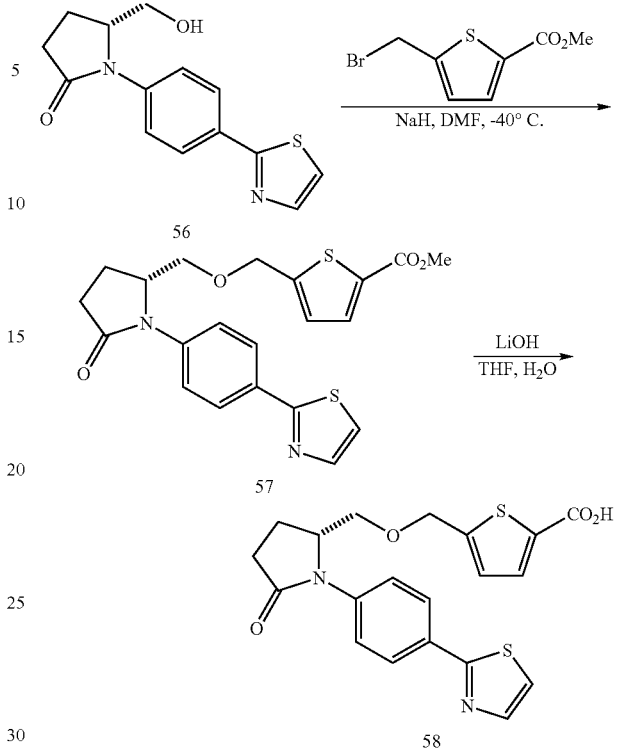

EXAMPLE 16

(R)-5-(((5-oxo-1-(4-(thiazol-2-yl)phenyl)pyrrolidin-2-yl)methoxy)methyl)thiophene-2-carboxylic acid (58)

Step 1. Arylation of 1 to Give 56

Potassium carbonate (800 mg, 5.79 mmol), copper(I) iodide (55 mg, 0.29 mmol) and N,N'-dimethylethylene diamine (62 µL, 0.58 mmol) were added sequentially to a solution of amide 1 (400 mg, 3.47 mmol) and 2-(4-bromophenyl)thiazole (for representative preparation, see Chemica Scripta 1985, 25(4), 295-299; 694 mg, 2.89 mmol) in MeCN (6.6 mL). The reaction flask was fitted with a reflux condenser, the mixture was degassed with nitrogen by evac/fill (5×) and then heated at reflux. After 18 hours, the mixture was cooled, diluted with EtOAc and filtered through celite, washing with excess EtOAc. The filtrate was concentrated in vacuo. The crude residue was purified on 40 g silica (CH₂Cl₂→15% MeOH/CH₂Cl₂, gradient) to afford 530 mg (67%) of 56.

Step 2. Alkylation of 56 to Give 57

Sodium hydride (60% dispersion in oil, 26 mg, 0.65 mmol) was added to a solution of alcohol 56 (120 mg, 0.44 mmol) at 0° C. and the mixture was allowed to warm to room temperature. After 20 minutes, the mixture was cooled to −40° C. and a solution of methyl 5-(bromomethyl)thiophene-2-carboxylate (125 mg, 0.53 mmol) in DMF (1.1 mL) was added via cannula. After 1 hours at −40° C. the reaction was quenched with 0.5 N HCl (15 mL) and extracted with EtOAc (3×30 mL). The combined extracts were washed with water (2×20 mL) and brine (20 mL) then dried (Na₂SO₄), filtered and concentrated in vacuo. The crude residue was purified on 12 g silica (hexanes→EtOAc, gradient) to afford 84 mg (45%) of 57.

Step 3. Saponification of 57 to Give 58

In accordance with the procedure of example 1, step 11, ester 57 (37 mg, 0.086 mmol) was converted into 20 mg (56%) of the title compound (58) after purification on 4 g silica (CH$_2$Cl$_2$→15% MeOH/CH$_2$Cl$_2$, gradient).

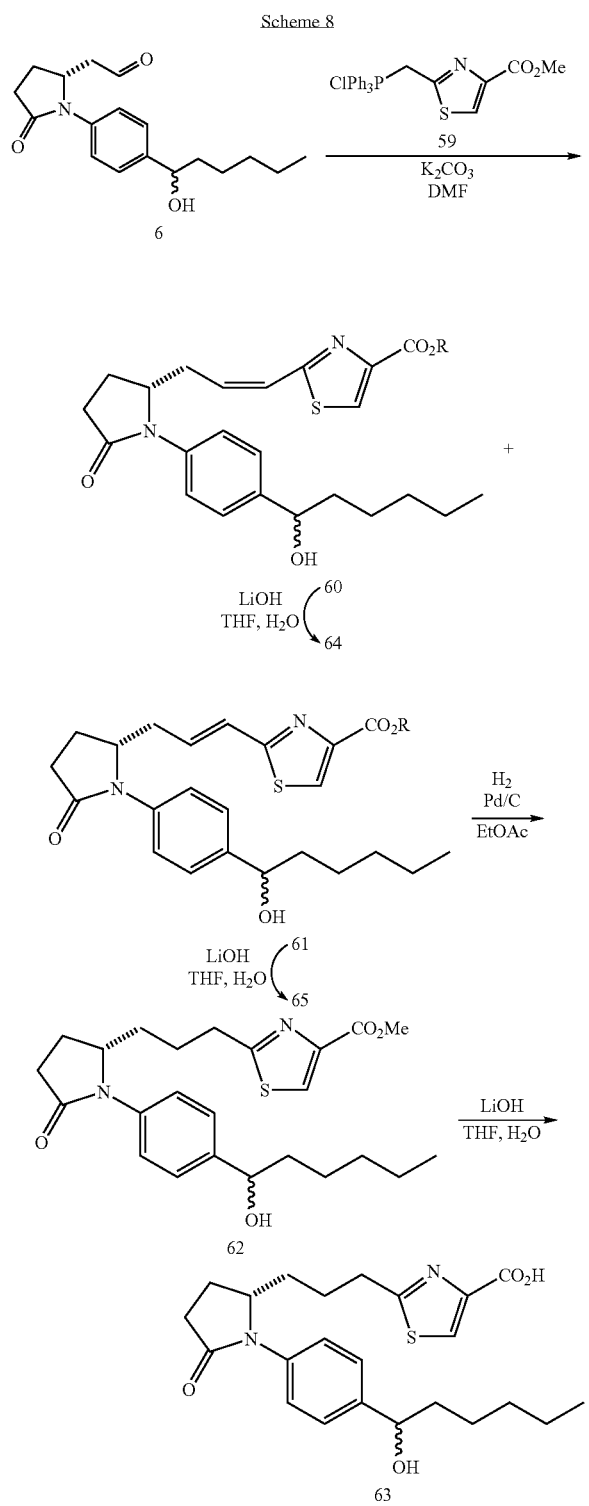

EXAMPLE 17

(S)-2-(3-(1-(4-(1-hydroxyhexyl)phenyl)-5-oxopyrrolidin-2-yl)propyl)thiazole-4-carboxylic acid (63)

Step 1. Wittig Reaction of 6 with Phosphonate 59 to Give 60 and 61

Potassium carbonate (256 mg, 1.85 mmol) was added to a solution of aldehyde 6 (Example 1, step 4, 160 mg, 0.37 mmol) and phosphonate 59 (prepared from known chloride (*Organic Process Research and Development*. 2001, 5, 37-44) by reaction with PPh$_3$ in refluxing toluene; 336 mg, 0.74 mmol) in DMF (3.7 mL) at 0° C., and the reaction mixture was allowed to warm to room temperature. After 4 days at room temperature, the mixture was diluted with water (35 mL) and extracted with EtOAc (3×35 mL). The combined extracts were washed with water (30 mL) and brine (35 mL) then dried (Na$_2$SO$_4$), filtered and concentrated in vacuo. The crude residue was purified on 12 g silica (35% EtOAc/hexanes→EtOAc, gradient) to afford 25 mg (15%) of cis-olefin 60 and 100 mg (61%) of trans-olefin 61.

Step 2. Hydrogenation of 61 to Give 62

Palladium on carbon (10 wt. %, 11 mg) was added to a solution of alkene 61 (46 mg, 0.10 mmol) in EtOAc (1.0 mL). A hydrogen atmosphere was established by evacuating and refilling with hydrogen (5×) and the mixture was stirred under a balloon of hydrogen. After 18 hours, the reaction was filtered through celite, washing with excess EtOAc. The filtrate was concentrated in vacuo. The crude residue was purified on 12 g silica (75% EtOAc/hexanes→EtOAc, gradient) to afford 34 mg (74%) of 62.

Step 3. Saponification of 62 to Give 63

In accordance with the procedure of example 1, step 11, ester 62 (34 mg, 0.086 mmol) was converted into 29 mg (88%) of the title compound (63).

EXAMPLE 18

(R,Z)-2-(3-(1-(4-(1-hydroxyhexyl)phenyl)-5-oxopyrrolidin-2-yl)prop-1-enyl)thiazole-4-carboxylic acid (64)

In accordance with the procedure of example 1, step 11, ester 60 (25 mg, 0.056 mmol) was converted into 11 mg (45%) of the title compound (64) after purification on 4 g silica (CH$_2$Cl$_2$→10% MeOH/CH$_2$Cl$_2$, gradient).

EXAMPLE 19

(R,E)-2-(3-(1-(4-(1-hydroxyhexyl)phenyl)-5-oxopyrrolidin-2-yl)prop-1-enyl)thiazole-4-carboxylic acid (65)

In accordance with the procedure of example 1, step 11, ester 61 (20 mg, 0.045 mmol) was converted into 16 mg (83%) of the title compound (65).

Scheme 9

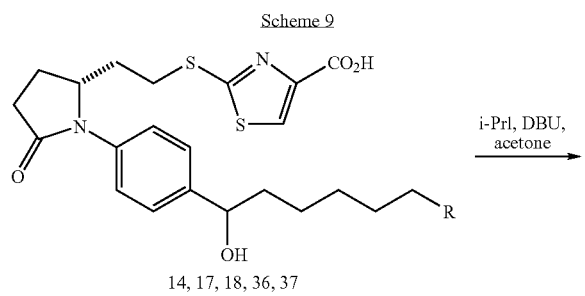

14, 17, 18, 36, 37 i-PrI, DBU, acetone →

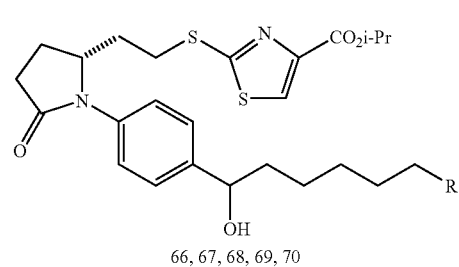

66, 67, 68, 69, 70

EXAMPLE 20

Isopropyl 2-(2-((2R)-1-(4-(1-hydroxyhexyl)phenyl)-5-oxopyrrolidin-2-yl)ethylthio)thiazole-4-carboxylic (66) 1,8-Diazabicyclo[5.4.0]undec-7-ene (DBU, 5.3 μL, 0.035 mmol) and 2-iodopropane (36 μL, 0.36 mmol) were added to a solution of acid 14 (8 mg, 0.018 mmol) in acetone (0.2 mL) at room temperature under nitrogen. After 4 days at room temperature, the solvent was removed under a stream of nitrogen. The residue was acidified with 1.0 N HCl (2 mL) extracted with EtOAc (3×10 mL). The combined organic phases was washed with brine (5 mL), dried ($Na_2SO_4$), filtered and concentrated in vacuo. Purification of the residue by flash column chromatography on 4 g silica ($CH_2Cl_2$→10% MeOH/$CH_2Cl_2$, gradient) afforded 8 mg (91%) of the title compound (66).

EXAMPLE 21

Isopropyl 2-(2-((2R)-1-(4-(1-hydroxyhexyl)phenyl)-5-oxopyrrolidin-2-yl)ethylthio)thiazole-4-carboxylate (67, from 17 and faster eluting diastereomer 15)

DBU (5.3 μL, 0.035 mmol) and 2-iodopropane (36 μL, 0.36 mmol) were added to a solution of acid 17 (8 mg, 0.018 mmol) in acetone (0.2 mL) at room temperature under nitrogen. After 18 hours at room temperature, the solvent was removed under a stream of nitrogen. The residue was diluted with water (2 mL) and acidified with 1.0 N HCl (2 mL) extracted with EtOAc (3×10 mL). The combined organic phases was washed with brine (5 mL), dried ($Na_2SO_4$), filtered and concentrated in vacuo. Purification of the residue by flash column chromatography on 4 g silica ($CH_2Cl_2$→15% MeOH/$CH_2Cl_2$, gradient) afforded 7 mg (80%) of the title compound (67).

EXAMPLE 22

Isopropyl 2-(2-((2R)-1-(4-(1-hydroxyhexyl)phenyl)-5-oxopyrrolidin-2-yl)ethylthio)thiazole-4-carboxylate (68, from 18 and slower eluting diastereomer 16)

In accordance with the procedure of example 21, acid 18 (8 mg, 0.018 mmol) was converted into 7.5 mg (86%) of the title compound (68).

EXAMPLE 23

Isopropyl 2-(2-((2R)-1-(4-(1-hydroxyheptyl)phenyl)-5-oxopyrrolidin-2-yl)ethylthio)thiazole-4-carboxylate (69, from 36 and faster eluting diastereomer 34)

In accordance with the procedure of example 21, acid 36 (8 mg, 0.017 mmol) was converted into 7 mg (80%) of the title compound (69).

EXAMPLE 24

Isopropyl 2-(2-((2R)-1-(4-(1-hydroxyheptyl)phenyl)-5-oxopyrrolidin-2-yl)ethylthio)thiazole-4-carboxylate (70, from 37 and slower eluting diastereomer 35)

In accordance with the procedure of example 21, acid 37 (8 mg, 0.017 mmol) was converted into 7 mg (80%) of the title compound (70).

In Vitro Testing

U.S. patent application Ser. No. 11/553,143, filed on Oct. 26, 2006, incorporated by reference herein, describes the methods used to obtain the in vitro data in the table below.

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| Chiral [structure] | 36 | 0.19 | 11 | NT | >10000 | NA | >10000 | 44 | >10000 | >10000 | >10000 |

| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| 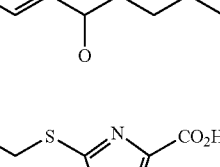 Chiral, faster eluting | 18 | 0.15 | 15 | NT | NA | NA | >10000 | 35 | NA | NA | >10000 |
| 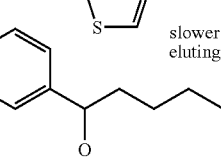 Chiral, slower eluting | 7 | 0.09 | 15 | NT | NA | NA | NA | 46 | NA | NA | 7171 |
| 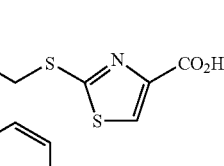 Chiral | 8 | 0.23 | 9 | NT | >10000 | NA | >10000 | 90 | NA | NA | >10000 |
| 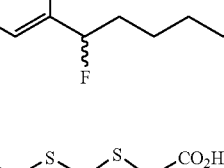 Chiral | 1797 | 4 | 389 | NT | >10000 | NA | NA | 11352 | NA | >10000 | >10000 |
| 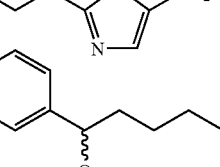 Chiral | 3 | 0.4 | 12 | >10000 | 6364 | NA | >10000 | 25 | NA | NA | 1565 |
| 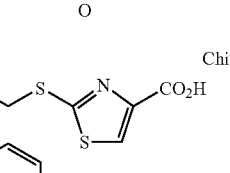 Chiral, faster eluting | 57 | 1.2 | 13 | | >10000 | NA | | 11 | NA | NA | 11933 |

-continued
| Structure | EP2 data | | | EP4 data | | Other Receptors (EC50 in nM) | | | | | |
|---|---|---|---|---|---|---|---|---|---|---|---|
| | flipr EC50 | cAMP EC50 | Ki | flipr EC50 | KI | hFP | hEP1 | hEP3A | hTP | hIP | hDP |
| 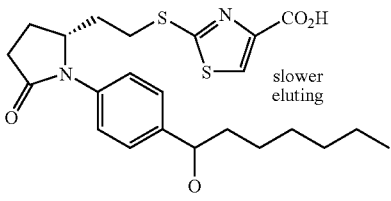 Chiral, slower eluting | 11 | 0.4 | 9 | 14638 | 9152 | NA | NA | 51 | NA | NA | 5320 |
| 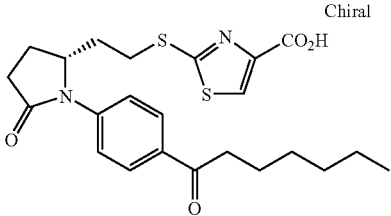 Chiral | 45 | 0.7 | 18 | >10000 | 3032 | NA | NA | 43 | NA | NA | 594 |
| 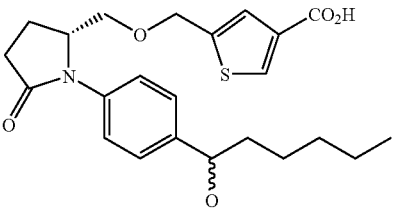 | 2242 | 5.5 | 448 | >10000 | | NA | NA | 1520 | NA | NA | NA |
| 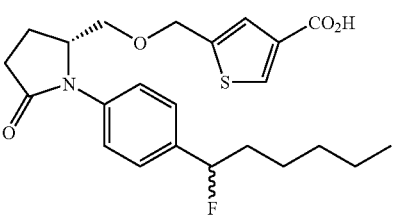 | 3854 | 7 | 256 | >10000 | | NA | NA | 1957 | NA | NA | NA |
| 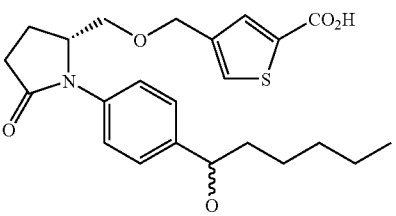 | 2534 | 18 | 784 | >10000 | | | | 1335 | | | |
| 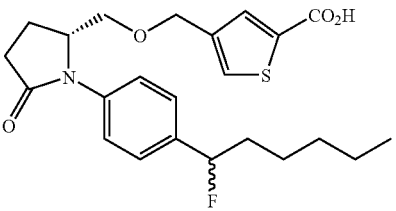 | 5005 | 40 | 1934 | >10000 | | | | 3410 | | | |

-continued

| Structure | | EP2 data | | | EP4 data | | Other Receptors (EC50 in nM) | | | | | |
|---|---|---|---|---|---|---|---|---|---|---|---|---|
| | | flipr EC50 | cAMP EC50 | Ki | flipr EC50 | KI | hFP | hEP1 | hEP3A | hTP | hIP | hDP |
| (pyrrolidinone-S-thiazole-CO2H with 4-(1-fluorohexyl)phenyl) | Chiral | 212 | 117 | 345 | >10000 | NA | NA | 503 | 14472 | NA | 16415 |
| (pyrrolidinone-S-thiazole-CO2H with 4-(1-hydroxyhexyl)phenyl) | Chiral | 284 | 120 | 355 | >10000 | NA | NA | 360 | 3887 | NA | 16001 |
| (pyrrolidinone-CH2-O-CH2-thiophene-CO2H with 4-thiazolylphenyl) | | 5889 | 38 | 215 | NA | >10000 | NA | NA | >10000 | NA | 4639 |
| (pyrrolidinone-propyl-thiazole-CO2H with 4-(1-oxohexyl)phenyl) | Chiral | 37 | 0.8 | 115 | NA | NA | | 42 | NA | NA | >10000 |
| (pyrrolidinone-vinyl-thiazole-CO2H with 4-(1-oxohexyl)phenyl) | Chiral | 17 | 0.75 | 43 | NA | NA | NA | 43 | NA | NA | 1850 |

-continued

| | EP2 data | | | EP4 data | | Other Receptors (EC50 in nM) | | | | | |
|---|---|---|---|---|---|---|---|---|---|---|---|
| | flipr | cAMP | | flipr | | | | | | | |
| Structure | EC50 | EC50 | Ki | EC50 | KI | hFP | hEP1 | hEP3A | hTP | hIP | hDP |
| Chiral | | 24 | 2177 | NA | NA | NA | NA | 2982 | >10000 | NA | >10000 |

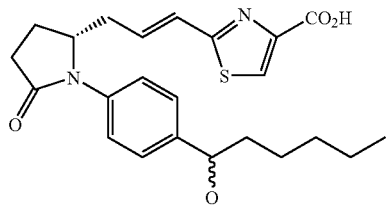

In Vivo Testing

U.S. Pat. No. 7,091,231 describes the methods used to carry out the tests reported below.

Isopropyl 2-(2-((2R)-1-(4-(1-hydroxyhexyl)phenyl)-5-oxopyrrolidin-2-yl)ethylthio)thiazole-4-carboxylate (66) was tested in normotensive dogs at 0.01%, dosing once daily for 5 days. The maximum intraocular pressure (IOP) decrease from baseline was 6.3 mmHg (39%) at 4 h; the maximum ocular surface hyperemia (OSH) score was 1.6 at 28 hours. This compound was also tested in laser-induced hypertensive monkeys, using one single day dose. At 0.01%, the maximum IOP decrease from baseline was 23 mmHg (61%) at 24 hours.

Isopropyl 2-(2-((2R)-1-(4-(1-hydroxyhexyl)phenyl)-5-oxopyrrolidin-2-yl)ethylthio)thiazole-4-carboxylate (67, from 17 and faster eluting diastereomer 15) was tested in normotensive dogs 2 different concentrations, dosing once daily for 5 days. At 0.01%, the maximum intraocular pressure (IOP) decrease from baseline was 6.9 mmHg (43%) at 78 h; the maximum ocular surface hyperemia (OSH) score was 2.0 at 26 hours. At 0.001%, the maximum intraocular pressure (IOP) decrease from baseline was 6.3 mmHg (38%) at 4 h; the maximum ocular surface hyperemia (OSH) score was 1.9 at 50 hours. This compound was also tested in laser-induced hypertensive monkeys, using one single day dose. At 0.01%, the maximum IOP decrease from baseline was 15 mmHg (43%) at 24 hours.

Isopropyl 2-(2-((2R)-1-(4-(1-hydroxyhexyl)phenyl)-5-oxopyrrolidin-2-yl)ethylthio)thiazole-4-carboxylate (68, from 18 and slower eluting diastereomer 16) was tested in normotensive dogs at 0.01%, dosing once daily for 5 days. The maximum intraocular pressure (IOP) decrease from baseline was 6.4 mmHg (41%) at 6 h; the maximum ocular surface hyperemia (OSH) score was 2.0 at 28 hours. This compound was also tested in laser-induced hypertensive monkeys, using one single day dose. At 0.01%, the maximum IOP decrease from baseline was 15 mmHg (43%) at 24 hours.

The invention claimed is:

1. A compound selected from:

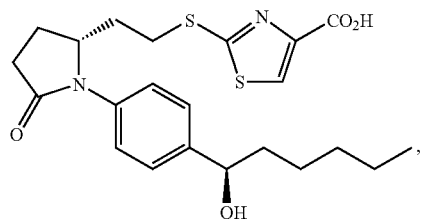

-continued

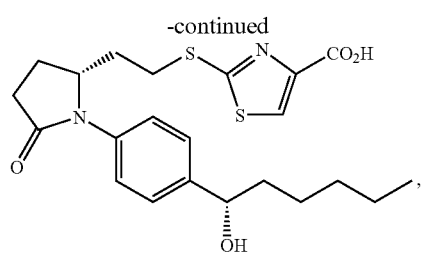

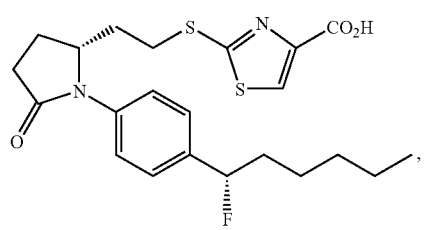

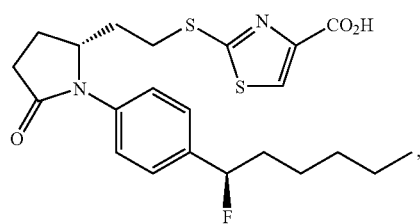

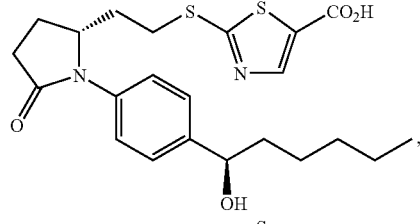

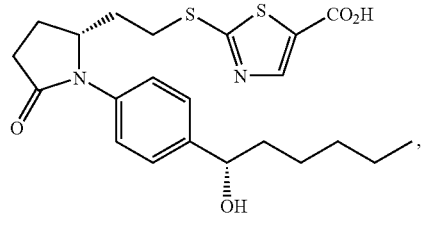

37
-continued
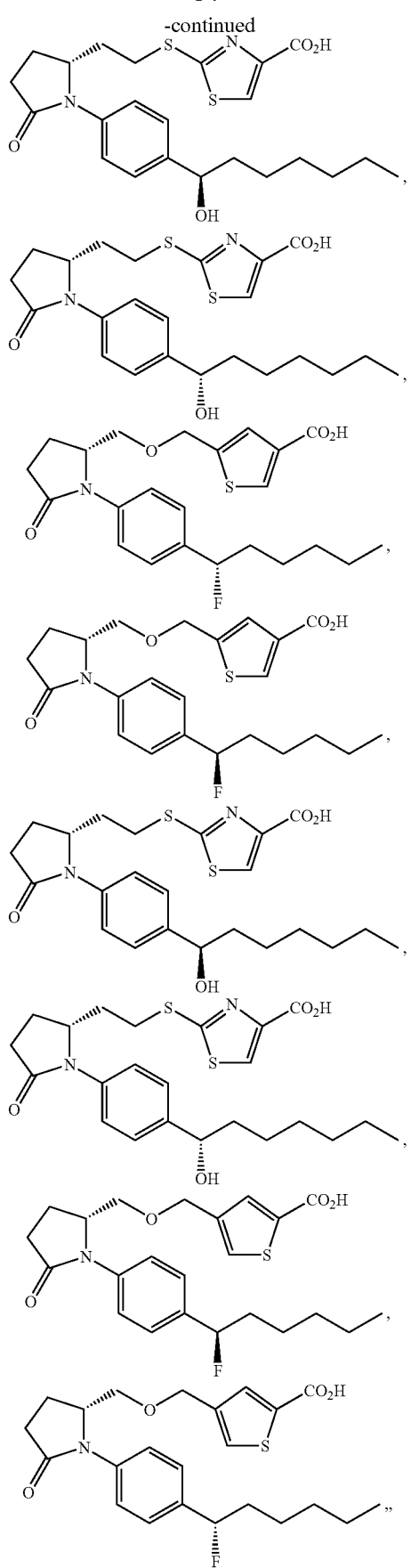
38
-continued
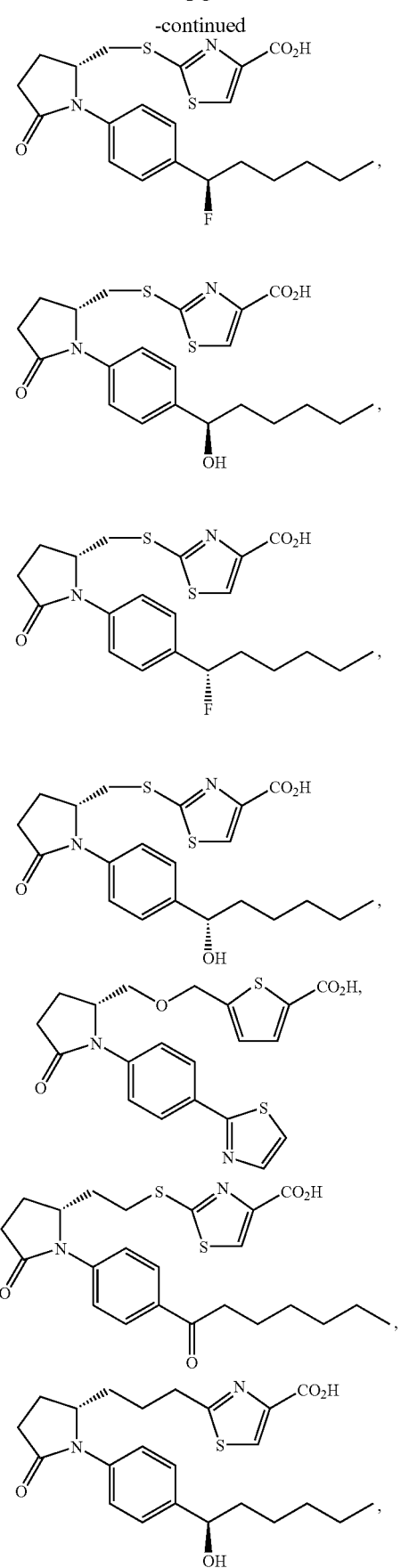

-continued
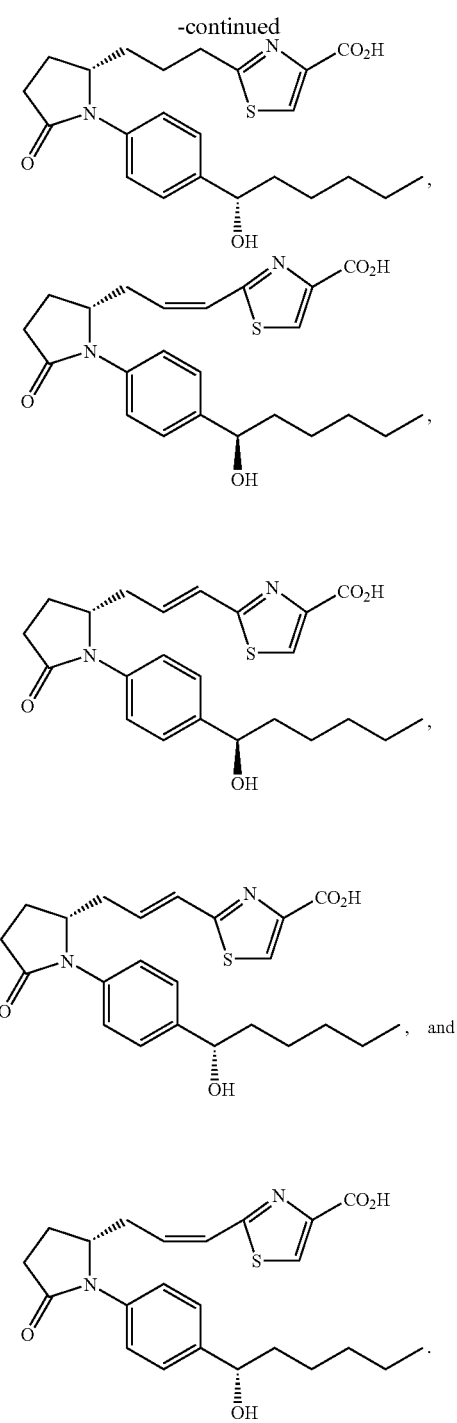
2. The compound of claim 1 having a structure:
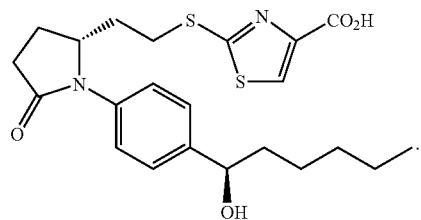
3. The compound of claim 1 having a structure:
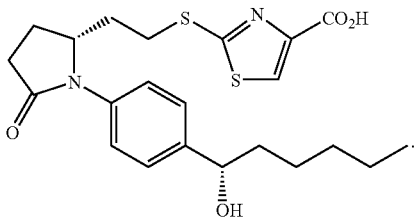
4. The compound of claim 1 having a structure:
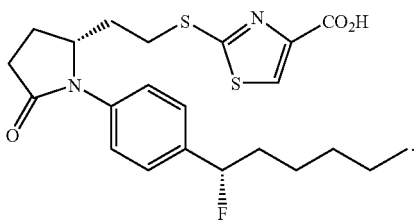
5. The compound of claim 1 having a structure:
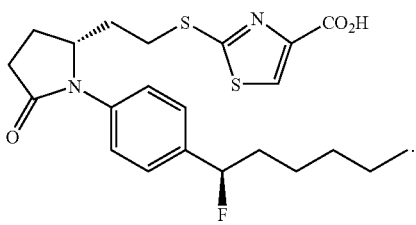
6. The compound of claim 1 having a structure:
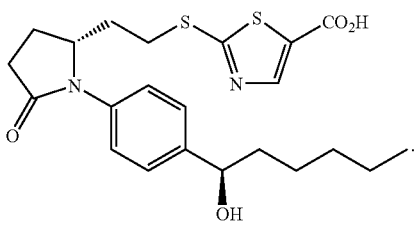
7. The compound of claim 1 having a structure:
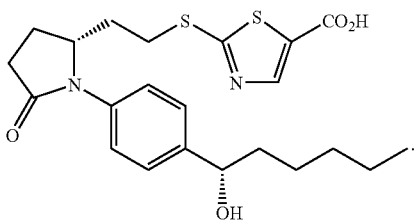

8. The compound of claim 1 having a structure:

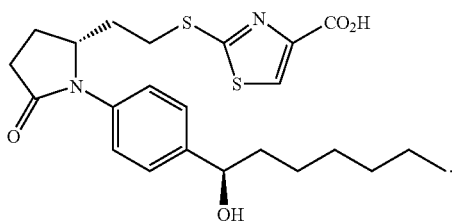

9. The compound of claim 1 having a structure:

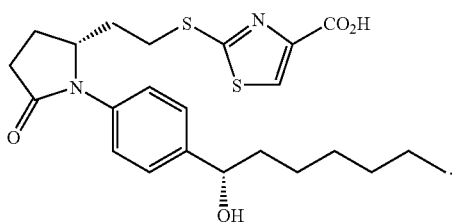

10. The compound of claim 1 having a structure:

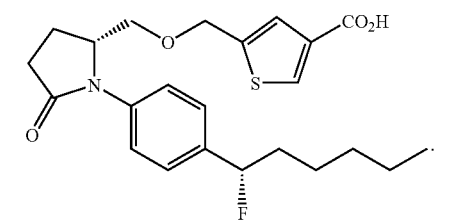

11. The compound of claim 1 having a structure:

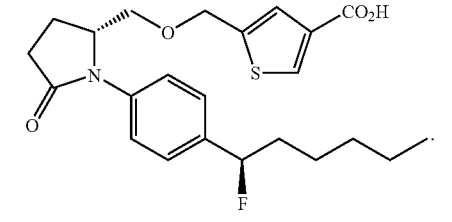

12. The compound of claim 1 having a structure:

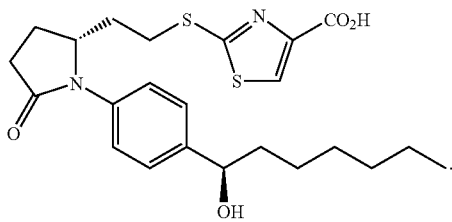

13. The compound of claim 1 having a structure:

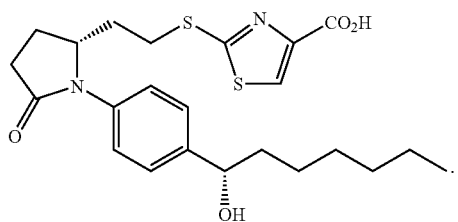

14. The compound of claim 1 having a structure:

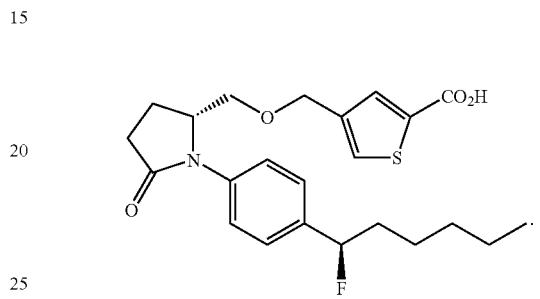

15. The compound of claim 1 having a structure:

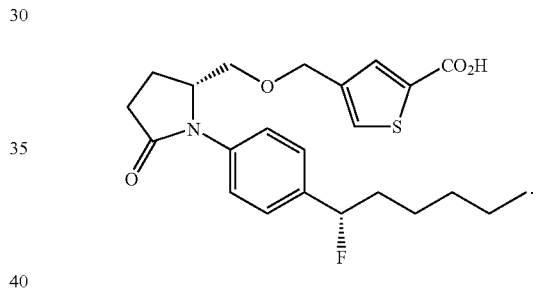

16. The compound of claim 1 having a structure:

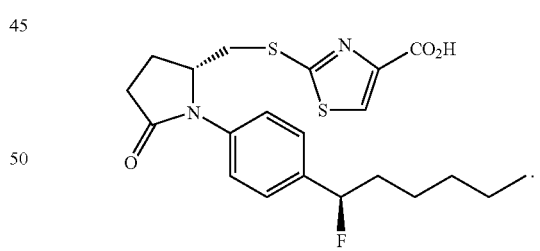

17. The compound of claim 1 having a structure:

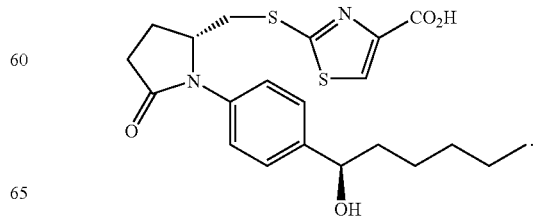

18. The compound of claim 1 having a structure:

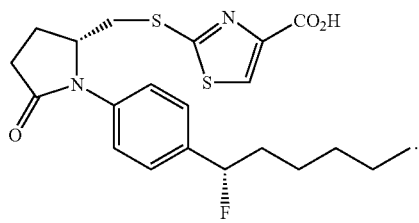

19. The compound of claim 1 having a structure:

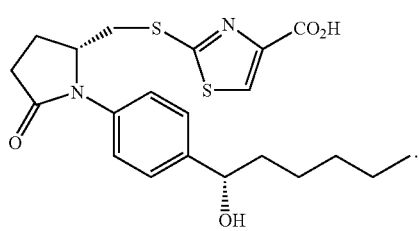

20. The compound of claim 1 having a structure:

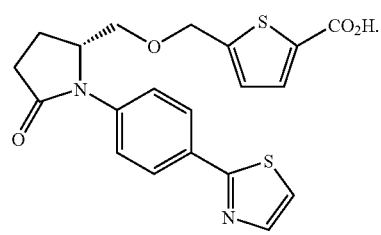

21. The compound of claim 1 having a structure:

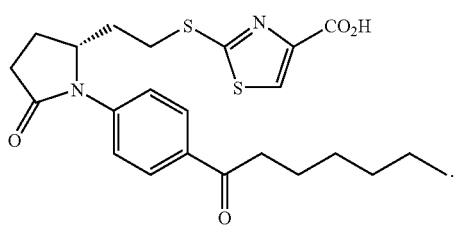

22. The compound of claim 1 having a structure:

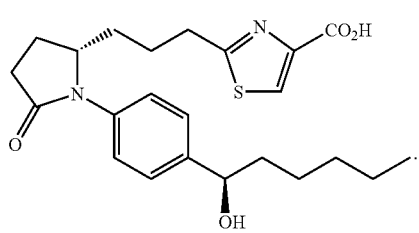

23. The compound of claim 1 having a structure:

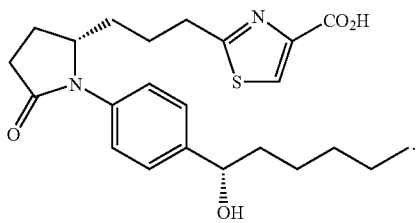

24. The compound of claim 1 having a structure:

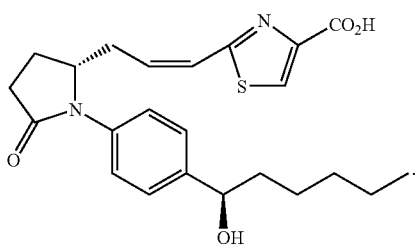

25. The compound of claim 1 having a structure:

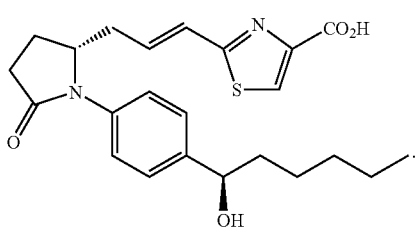

26. The compound of claim 1 having a structure:

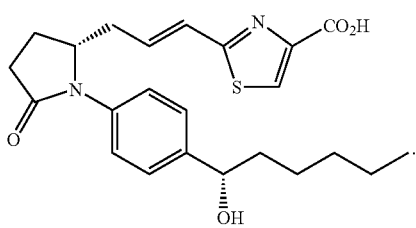

27. The compound of claim 1 having a structure:

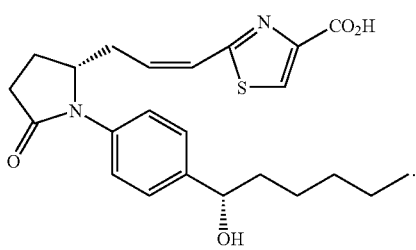

* * * * *